US010736981B2

(12) United States Patent
Scheuber et al.

(10) Patent No.: US 10,736,981 B2
(45) Date of Patent: Aug. 11, 2020

(54) ARRANGEMENT FOR PERFORMING A DECONTAMINATION PROCESS BY MEANS OF A DECONTAMINATION AGENT INTRODUCED INTO A CONTAINMENT

(71) Applicant: Skan AG, Allschwil (CH)

(72) Inventors: Olivera Scheuber, Schönenbuch (CH); Volker Sigwarth, Sisseln (CH)

(73) Assignee: SKAN AG, Allschwil (CH)

( * ) Notice: Subject to any disclaimer, the term of this patent is extended or adjusted under 35 U.S.C. 154(b) by 268 days.

(21) Appl. No.: 15/566,921

(22) PCT Filed: Apr. 11, 2016

(86) PCT No.: PCT/CH2016/000061
§ 371 (c)(1),
(2) Date: Oct. 16, 2017

(87) PCT Pub. No.: WO2016/165031
PCT Pub. Date: Oct. 20, 2016

(65) Prior Publication Data
US 2018/0110891 A1    Apr. 26, 2018

(30) Foreign Application Priority Data
Apr. 16, 2015   (EP) ..................... 15405029

(51) Int. Cl.
*A61L 2/00*   (2006.01)
*A61L 9/00*   (2006.01)
*A61L 2/20*   (2006.01)

(52) U.S. Cl.
CPC ................. *A61L 2/208* (2013.01); *A61L 2/20* (2013.01); *A61L 2202/122* (2013.01); *A61L 2202/13* (2013.01)

(58) Field of Classification Search
CPC . A61L 2/00; A61L 2/0094; A61L 2/16; A61L 2/20; A61L 2/22; A61L 9/00; A61L 9/015; A61L 2202/11; A61L 2209/13
(Continued)

(56) References Cited

U.S. PATENT DOCUMENTS 5,711,705 A   1/1998   Krainiak et al.
5,792,435 A   8/1998   Mueller et al.
(Continued)

FOREIGN PATENT DOCUMENTS

EP   2283874 A1   2/2011
EP   2692848 A1   2/2014
(Continued)

OTHER PUBLICATIONS

International Search Report of the International Searching Authority, along with its English translation, dated Aug. 12, 2016, issued in connection with International Application No. PCT/CH2016/000061 (18 pages).
(Continued)

*Primary Examiner* — Monzer R Chorbaji
(74) *Attorney, Agent, or Firm* — McCarter & English, LLP

(57) ABSTRACT

Performing a decontamination process by introducing a decontamination agent into a first containment, the first containment is being surrounded by a housing having a primary inlet for admitting a gas medium into the first containment, and a primary outlet for discharging the gas medium from the first containment. The primary outlet leads to an area external to the first containment, into the open atmosphere, or to a second containment and has a gas-technology connection to a first catalyst unit through which the gas medium flows. By means of the at least first catalyst unit, the decontamination agent, which is introduced into the
(Continued)

Figure 1:
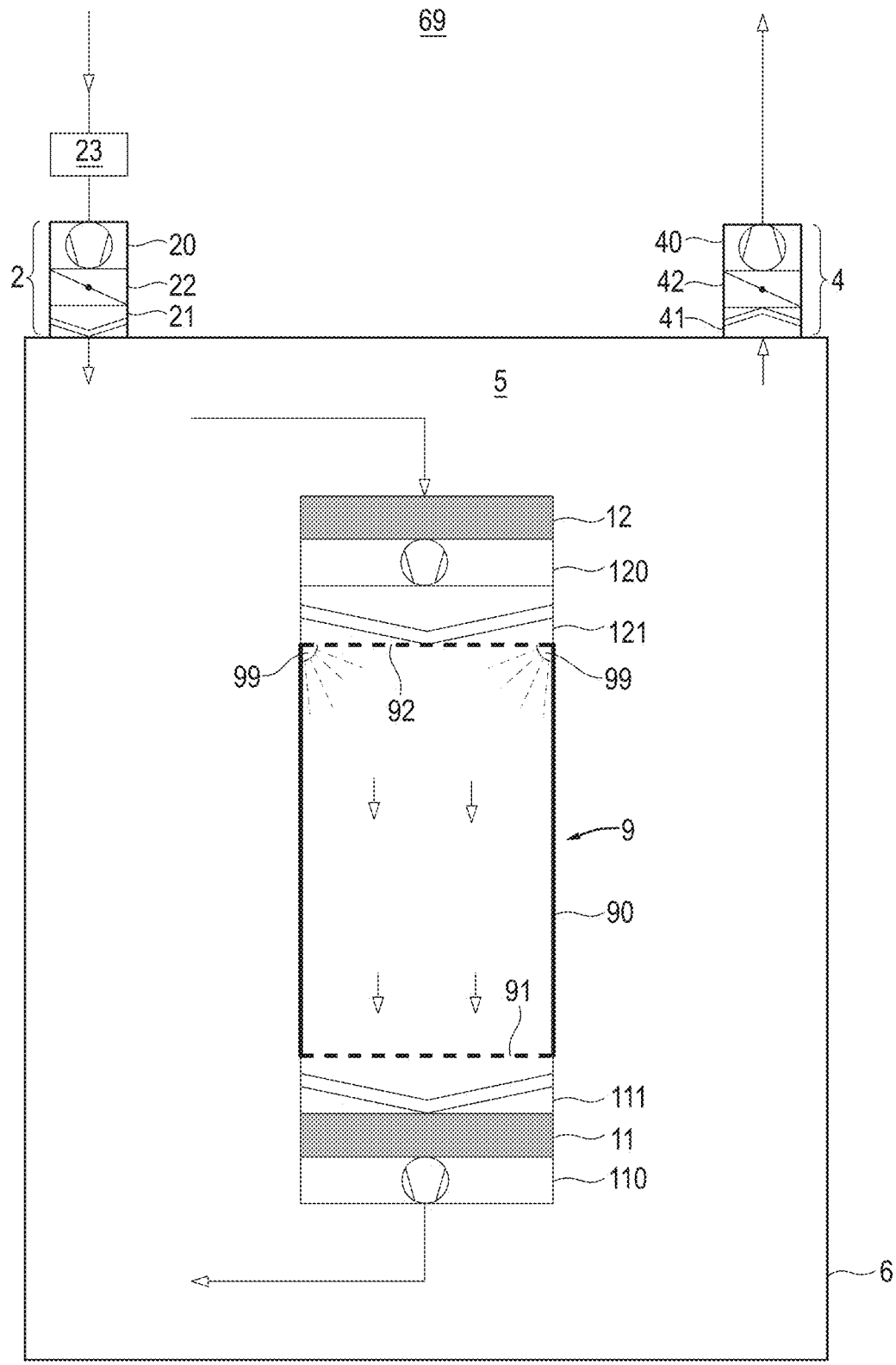

first containment during the decontamination process and enters with the gas medium into the area, open atmosphere or the second containment, can be split into non-critical components and degraded to a non-critical residual concentration.

24 Claims, 8 Drawing Sheets

(58) Field of Classification Search
USPC .................................. 422/27, 292, 305–306
See application file for complete search history.

(56) References Cited

U.S. PATENT DOCUMENTS

| | | |
|---|---|---|
| 6,010,400 A | 1/2000 | Krainiak et al. |
| 2010/0189607 A1 | 7/2010 | Yokoi et al. |
| 2011/0058986 A1* | 3/2011 | Yokoi .................. A61L 2/0094 422/111 |

FOREIGN PATENT DOCUMENTS

| | | |
|---|---|---|
| WO | 01/21223 A1 | 3/2001 |
| WO | 02/11774 A1 | 2/2002 |
| WO | 2005/118005 A2 | 12/2005 |
| WO | 2008/116341 A2 | 10/2008 |
| WO | 2011/085735 A1 | 7/2011 |
| WO | 2013/003967 A1 | 1/2013 |

OTHER PUBLICATIONS

Written Opinion of the International Searching Authority dated Aug. 12, 2016, issued in connection with International Application No. PCT/CH2016/000061 (19 pages).

* cited by examiner

ARRANGEMENT FOR PERFORMING A DECONTAMINATION PROCESS BY MEANS OF A DECONTAMINATION AGENT INTRODUCED INTO A CONTAINMENT

RELATED APPLICATIONS

This application is a U.S. National Phase Application under 35 U.S.C. §371 of International Application No. PCT/CH2016/000061 filed Apr. 11, 2016, which claims the benefit of European Patent Application No. 15405029.8 filed on Apr. 16, 2015, the entire disclosures of which are incorporated by reference herein.

FIELD OF THE INVENTION

The present invention relates to an arrangement for performing a decontamination process by means of a decontamination agent introduced into a first containment. The first containment has a housing, a primary inlet for entry of a gaseous medium and a primary outlet for exit of the gaseous medium. Containments are in particular isolators, for example for the pharmaceutical-chemical industry, locks and safety work stations, for example for microbiological operations or operations involving toxic entities. The term further comprehends all types of restricted access barrier systems (RABSs), including mobile and stationary kinds, such as means of transport and rooms for treatment, isolation and/or diagnostics of patients, and also production rooms and laboratories.

PRIOR ART

U.S. Pat. Nos. 5,711,705 and 6,010,400 relate to the design and construction of a safety work station and also a method of operating the safety work station, each in alternative embodiments. In normal operation, a laminar airstream is directed downwardly through the process chamber whereabove an upper plenum containing a filter assembly is provided. The filter assembly contains a catalyst to degrade the preferred $H_2O_2$ decontaminant into $H_2O$ and $O_2$. A main duct, in which a blower and control valves are installed, extends away from the plenum positioned below the process chamber and opens into the upper plenum. The main duct has branched away from it a bypass duct which runs parallel with the main duct and is internally fitted with a decontamination agent vaporizer. A secondary duct, which contains a further control valve, branches off from the main duct at a point above the bypass duct and opens into the process chamber near the bottom thereof. In normal operation, the airstream is driven by the blower to circulate through the main duct, the filter assembly in the upper plenum, the process chamber and the lower plenum before reentering the main duct. During a purge phase, the circulating airstream enriched with $H_2O_2$ is routed through the filter assembly and the catalyst region thereof, where the decontamination agent is broken down. In the course of the decontamination phase, the bypass duct, containing the vaporizer, is taken into operation in order that the circulating air, which otherwise flows through the main duct, may be enriched with $H_2O_2$ vapor. The various control valves can be actuated to feed the $H_2O_2$-bearing gas mixture into the process chamber via the secondary duct either directly or initially through the filter assembly—without passing through the separate catalyst region. During the entire decontamination phase, the catalyst stays delimited in air flow terms from the installation room surrounding the safety work station.

U.S. Pat. No. 5,792,435 describes a containment having a process chamber for ware to be microbiologically decontaminated therein, such as a batch of surgical instruments or pharmaceutical receptacles, according to which it was common practice for the preferred decontamination agent mixture of air as carrier gas and a vaporized, for example 35% strength, aqueous $H_2O_2$ solution to be sucked out of the process chamber and blown through a filter into the atmosphere where the $H_2O_2$ molecules disintegrate into $H_2O$ and $O_2$. The gas volume removed from the process chamber was replaced by freshly conditioned decontamination agent gas mixture introduced into the process chamber. To reduce the burden for conditioning fresh decontamination agent gas mixture, U.S. Pat. No. 5,792,435 proposes thereagainst that the spent gas mixture, quasi polluted out of the process chamber be sucked off via a converter comprising a catalyst disposed therein, where the breakdown of the $H_2O_2$ molecules takes place in hastened form, then to segregate off the moisture, then for the carrier gas thus dried to be preheated, routed via a vaporizer and be re-enriched with $H_2O_2$ vapor and returned into the process chamber. The carrier gas is thus recirculated in a closed circuit. Sensors, controllable valves and a central control unit are used to monitor proper operation. Again, the containment is in air flow terms delimited from the surroundings during decontamination by closed control valves.

WO 01/21223 A1 discloses a method and the related apparatus for decontaminating a containment having two pipework branches parallel thereto. One unlockable, primary pipework branch is provided for importing a vapor mixture enriched with decontamination agent, typically $H_2O_2$. Control means are provided for controlling the imported amount, the temperature and the soaking time of the decontamination agent. The purge phase involves a switch to operation through the secondary pipework branch, which contains a catalytic converter for degrading the decontamination agent in the purge stream, a dehumidifier and a heating device. The purge air treated in this way in the secondary pipework branch is recirculated directly back into the containment until the $H_2O_2$ degradation out of the purge air has reached the prescribed extent. To drive the air circulation, either a separate blower is provided in either pipework branch, or the effect of a single blower is alternatable between the two pipework branches by means of a control element.

WO 02/11774 A1 describes a method of hastening a purge phase for exporting the decontamination agent, preferably $H_2O_2$, out of an isolator. Under normal operating conditions, fresh air conditioned along a first flow path flows at a first rate as a laminar stream through the isolator, exiting the latter via an outlet as spent air in cleaned form. This requires the inflow of fresh air and the outflow of spent air to be controlled to equal flow rates in order to maintain a defined pressure in the isolator. To carry out a decontamination phase, $H_2O_2$ vapor is passed into the isolator along the first flow path. After decontamination has taken place, the $H_2O_2$ has to be exported in a purge phase as rapidly as possible and at minimum cost and inconvenience for air conditioning. To this end, purge air is circulated through the isolator via a second flow path at a multiplied flow rate, a catalyst disposed on this second flow path breaking down the $H_2O_2$ in the purge air, i.e., after its catalytic treatment, the purge air is again fed directly to the isolator. The purging cycle is continued until the degradation of $H_2O_2$ has got to below a maximum allowable concentration.

OBJECT OF THE INVENTION

In relation to the prior art, the invention addresses the problem of providing an arrangement for performing a decontamination process by means of a decontamination agent introduced into a first containment with appreciably reduced cost and inconvenience for air conditioning. The problem addressed by the invention is further that of reducing the deployment of control valves for gastight closure of the containment and also of process management control means. The problem addressed by the present invention is further that of providing, as a significant apparatus part of the arrangement, a more efficient catalytic unit for breaking down the decontamination agent introduced into a containment for the purpose of a decontamination process. Altogether, therefore, the economics of such arrangements in relation to the control engineering equipment requirements shall be improved.

SUMMARY OF THE INVENTION

The In the arrangement for performing a decontamination process by means of a decontamination agent introduced into a first containment, the first containment has a housing, the housing has a primary inlet for entry of a gaseous medium into the first containment and has a primary outlet for exit of the gaseous medium out of the first containment. The primary outlet of the first containment leads to an area external to the first containment or into the open atmosphere or to a second containment. At least the primary outlet is in gas communication with a first catalytic unit permeated by the gaseous medium. The decontamination agent introduced into the first containment during the decontamination process and entering with the gaseous medium into the area or the open atmosphere or a second containment is cleavable into uncritical components, and degradable down to an uncritical residual concentration, by the at least first catalytic unit. At least during the period in which there is a critical concentration of the decontamination agent in the first containment, the first containment is at all times gas pervious through the at least first catalytic unit to the area or to the open atmosphere or to the second containment.

Particular embodiments of the invention will now be defined: The primary inlet of the first containment may lead to an area external to the first containment or into the open atmosphere or to a second containment. The primary inlet is in gas communication with a second catalytic unit permeated by the gaseous medium. The decontamination agent introduced into the first containment during the decontamination process and entering with the gaseous medium into the area or the open atmosphere or a second containment is cleavable into uncritical components, and degradable down to an uncritical residual concentration, by the first and the second catalytic units. At least during the period in which there is a critical concentration of the decontamination agent in the first containment, the first containment is at all times gas pervious through the first and second catalytic units to the area or to the open atmosphere or to the second containment.

At least the first catalytic unit is assigned a first filter or at least the second catalytic unit is assigned a second filter. The pairings between the first catalytic unit and the first filter and between the second catalytic unit and the second filter are assigned respectively a first and a second blower.

The first containment with its housing is surrounded by a duct wall having a secondary outlet and a secondary inlet to form a circulating air duct having fluidic communication from the primary outlet to the primary inlet and to the secondary outlet and also from the secondary inlet to the primary inlet. The first catalytic unit is connected to the secondary outlet, and the second catalytic unit is connected to the secondary inlet.

The first catalytic unit is assigned the first filter and the first blower. The second catalytic unit is assigned the second filter and the second blower. At least one third filter is connected to the primary inlet. At least one third blower is arranged to convey out of the circulating air duct, through the at least one third filter and into the first containment. The at least one third blower aspirates a proportion of the gaseous medium flowing out of the primary outlet of the first containment for recirculation through the primary inlet into the first containment. By contrast, the first blower aspirates a proportion of the gaseous medium flowing out of the primary outlet of the first containment for conveying into the area via the first catalytic unit. A make-up flow through the secondary inlet replaces the gas volume removed via the first blower. At least one additional filter is connected between the primary outlet and the circulating air duct, wherein preferably at least one additional blower is connected to the at least one additional filter. The pairing between the at least one third filter and the at least one third blower is assigned a third catalytic unit.

Alternatively, the first containment with its housing is surrounded by a duct wall having a secondary outlet and a secondary inlet to form a circulating air duct having fluidic communication from the primary outlet to the primary inlet and to the secondary outlet and also from the secondary inlet to the primary inlet. The secondary outlet has connected to it the first filter which is assigned the first catalytic unit for gaseous medium to flow through into the area. The secondary inlet has connected to it the second filter which is assigned the second catalytic unit for gaseous medium to flow through out of the area. A third filter is connected to the primary inlet. A third blower is provided for conveying through the secondary inlet out of the area and out of the circulating air duct and through the third filter into the first containment. The third blower further conveys proportions of the gaseous medium flowing out of the primary outlet of the first containment and routed via the circulating air duct to flow respectively back into the first containment and through the secondary outlet to the area. Preferably at least one additional filter is connected to the primary outlet. Advantageously a third catalytic unit is disposed in the circulating air duct.

The area is delimited by a surrounding structure from a surrounding environment. The area has connected to it a feed air unit for importing conditioned fresh air into the area and also an exit air unit for exporting exit air out of the area.

In a subsequent alternative embodiment, the area subdivides into a plurality of space cells, wherein each space cell is delimited by its particular surrounding structure from a surrounding environment. The space cells are connected by a duct grid to the first containment in parallel or series. At least one air supply unit for circulating the gaseous medium through the first containment and the space cells is installed in the duct grid. At least one first filter is disposed between the primary outlet and one side of the first catalytic unit wherethrough gaseous medium flowing back out of the first containment passes into the duct grid. And/or at least one second filter is disposed between the primary inlet and one side of a second catalytic unit wherethrough gaseous medium passes out of the duct grid into the first e containment. The air supply unit comprises a supply blower, a supply filter and a conditioning unit. A feed air unit aspirating gaseous medium out of the open atmosphere serves to import fresh air into the duct grid and an exit air unit is connected to the duct grid and serves to export exit air into the open atmosphere.

In the case of a parallel connection:
a) an outlet duct from the first catalytic unit and from each space cell opens into a return duct which leads to the air supply unit; and
b) an inlet duct extends in each case to the second catalytic unit and to each space cell from a forerun duct emanating from the air supply unit. In a series connection by contrast:
a) a communicating duct extends from the first catalytic unit to a neighboring space cell and also between pairs of neighboring space cells and a communicating duct from a rearmost space cell opens into the return duct leading to the air supply unit; and
b) a separate communicating duct emanates from the air supply unit to extend to the second catalytic unit.

In a further alternative embodiment, the first containment, which is for performing a decontamination process with decontamination agent to be introduced, has an opening in its housing, a further catalytic unit is installed in said opening. The further catalytic unit opens into the second containment or the area or the open atmosphere. Again, at least during the period in which there is a critical concentration of the decontamination agent in the first containment, the first containment is at all times gas pervious through the further catalytic unit to the second containment or to the area or to the open atmosphere. The further catalytic unit is assigned a further filter at least aside the first containment or the second containment or the area or the open atmosphere. Advantageously the pairing between further catalytic unit and the at least one further filter may have the shape of a door which can be opened to transfer ware between the first containment and the second containment or the area or the open atmosphere.

Gaseous medium of toxic character exiting from the first catalytic unit does not have any access into the area but passes via an exit air duct to the exit air unit which includes a filter to retain the toxic particles and opens into the open atmosphere.

Containments are deemed to be in particular:
a) isolators, for example for the pharmaceutical-chemical industry, locks and safety work stations, for example for microbiological operations or operations involving toxic entities; and
b) restricted access barrier systems so-called RABSs, including mobile and stationary kinds, such as means of transport and for treatment of patients, and also production rooms and laboratories.

The decontamination agent used:
a) has a sporicidal effect which causes at least a 3-log reduction;
b) preferably passes in aerosol form into the containment, and
c) preferably is hydrogen peroxide [$H_2O_2$] or nitrogen dioxide [$NO_2$] or peroxy acetic acid [$C_2H_4O_3$] or a mixture of hydrogen peroxide [$H_2O_2$] and peroxy acetic acid [$C_2H_4O_3$].

The decontamination agent in the gaseous medium entering the area or the second containment or into the open atmosphere has an uncritical concentration of non-degraded decontamination agent amounting to less than 0.5 ppm, whereas a concentration above 1.0 ppm is defined as critical. Preferably the attained uncritical concentration of non-degraded decontamination agent is not more than 0.1 ppm.

In a first configuration, the at least first catalytic unit and, if respectively present, preferably also the second, third and further catalytic units have at least one catalytic element consisting of:
a) a carrier material formed from aluminum ceramic or activated carbon; and
b) a catalytically active component applied to the carrier material by chemical plating and taking the form of nanoparticles formed from silver or silver oxide or a mixture of silver and silver oxide.

The catalytically active component comprises from 0.05 wt % up to 0.5 wt %, preferably at 0.1 wt %, of the carrier material in the at least one catalytic element. The at least one catalytic element has a catalytically effective surface area ranging up to 320 $m^2$ per gram of catalyst material used, being the combination of carrier material plus applied catalytically active component. The specific surface area [$m^2$ per gram] of the catalyst material used, being the combination of carrier material plus applied catalytically active component, is not decreased by the applied nanoparticles in relation to the specific surface area [$m^2$ per gram] of the carrier material alone, before application of nanoparticles.

In a second configuration, the at least first catalytic unit and, if respectively present, preferably also the second, third and further catalytic units have at least two different catalytic elements, wherein the catalytic elements are constituted such that their respective highest efficiency in cleaving the decontamination agent occurs in different concentration ranges of the decontamination agent.

The at least two different catalytic elements of the catalytic units are formed by:
a) different catalytically active components applied to identical carrier material by chemical plating; and/or
b) identical catalytically active component applied to different carrier materials by chemical plating.

A first catalytic element of the at least two different catalytic elements has aluminum ceramic or activated carbon as carrier material and manganese oxide or Prussian Blue [iron(III) hexacyanidoferrate(II/III)] as catalytically active component applied to the carrier material in the form of nanoparticles. By contrast, a second catalytic element of the at least two different catalytic elements has aluminum ceramic or activated carbon as carrier material and silver or silver oxide or a mixture of silver and silver oxide applied as catalytically active component to the carrier material in the form of nanoparticles.

Manganese oxide or Prussian Blue [iron(III) hexacyanidoferrate(II/III)] is employed as catalytically active component for a first catalytic element to degrade decontamination agent in the range of a first concentration. However, silver or silver oxide or a mixture of silver and silver oxide is employed as catalytically active component for a second catalytic element to degrade decontamination agent in the range of a second concentration, which is lower than the first concentration.

The second configuration of the catalytic unit is likewise such that:
a) the catalytically active component comprises from 0.05 wt % up to 0.5 wt %, preferably at 0.1 wt %, of the carrier material in the particular catalytic element;
b) the particular catalytic element has a catalytically effective surface area ranging up to 320 $m^2$ per gram of carrier material plus applied catalytically active component; and
c) the specific surface area [$m^2$ per gram] of the catalyst material used, being the combination of carrier material plus applied catalytically active component, is not decreased by the applied nanoparticles in relation to the specific surface area [m² per gram] of the carrier material alone, before application of nanoparticles.

BRIEF DESCRIPTION OF THE ATTACHED DRAWINGS

Figure 2:
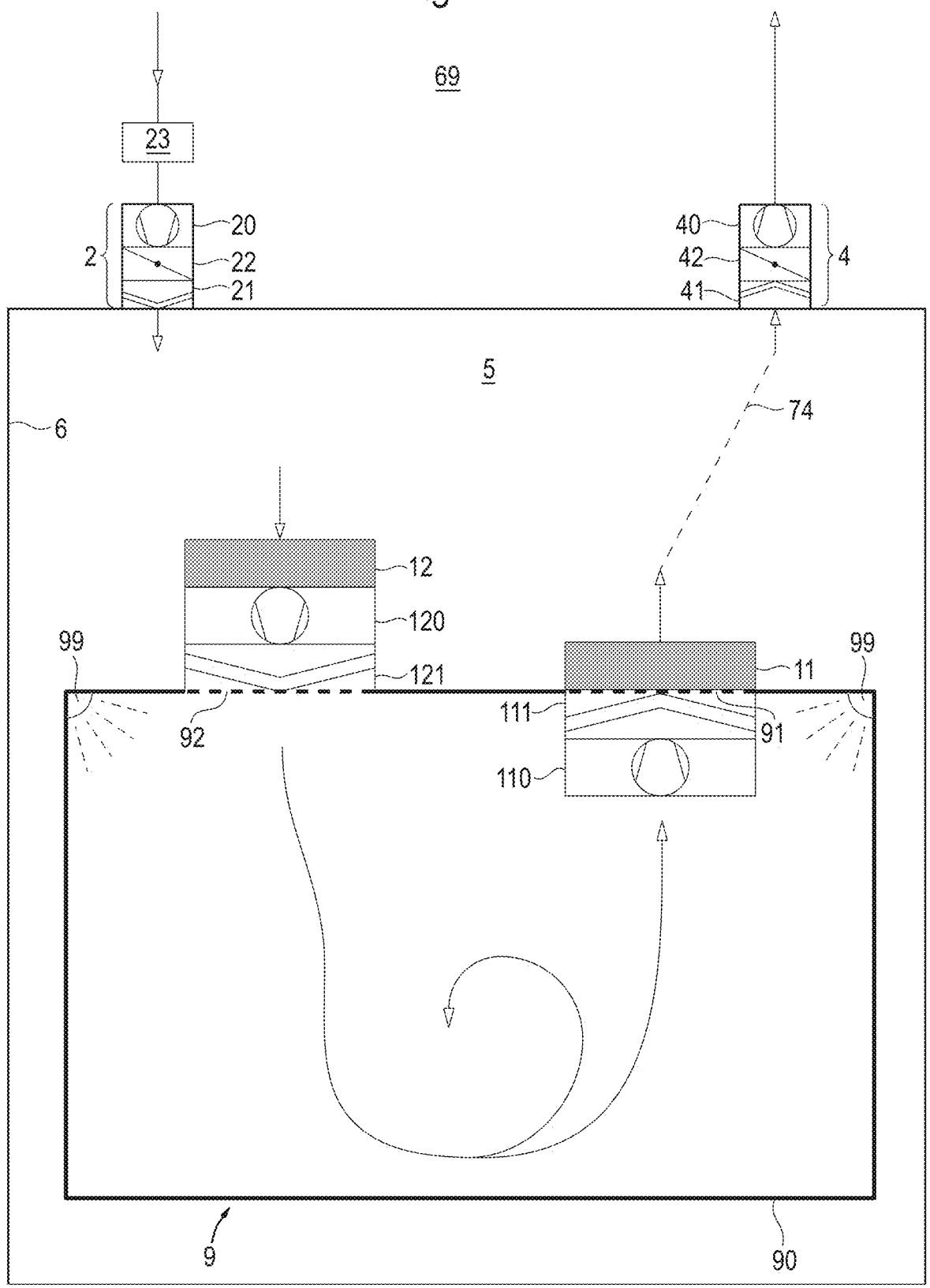
Figure 3:
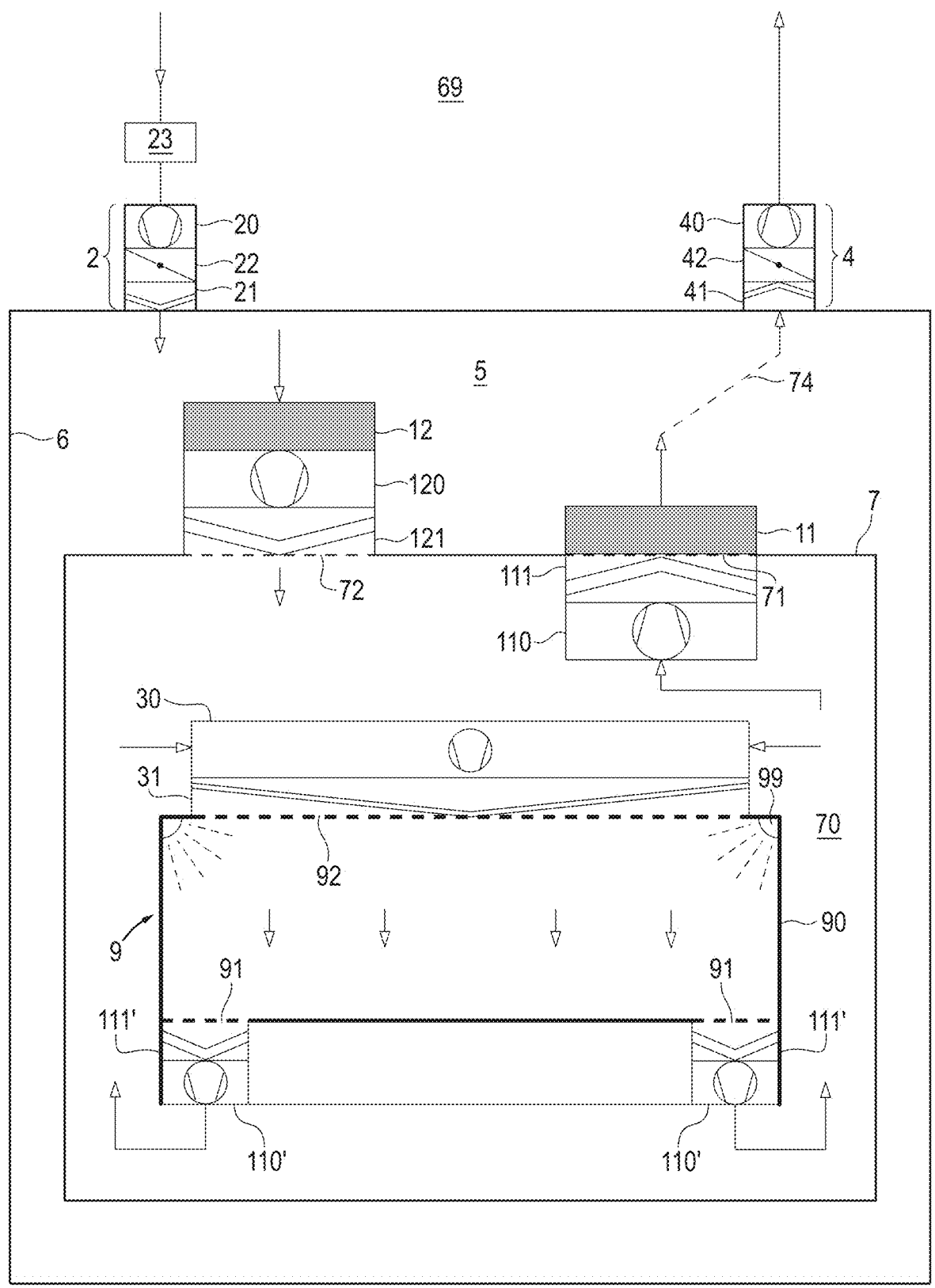
Figure 4:
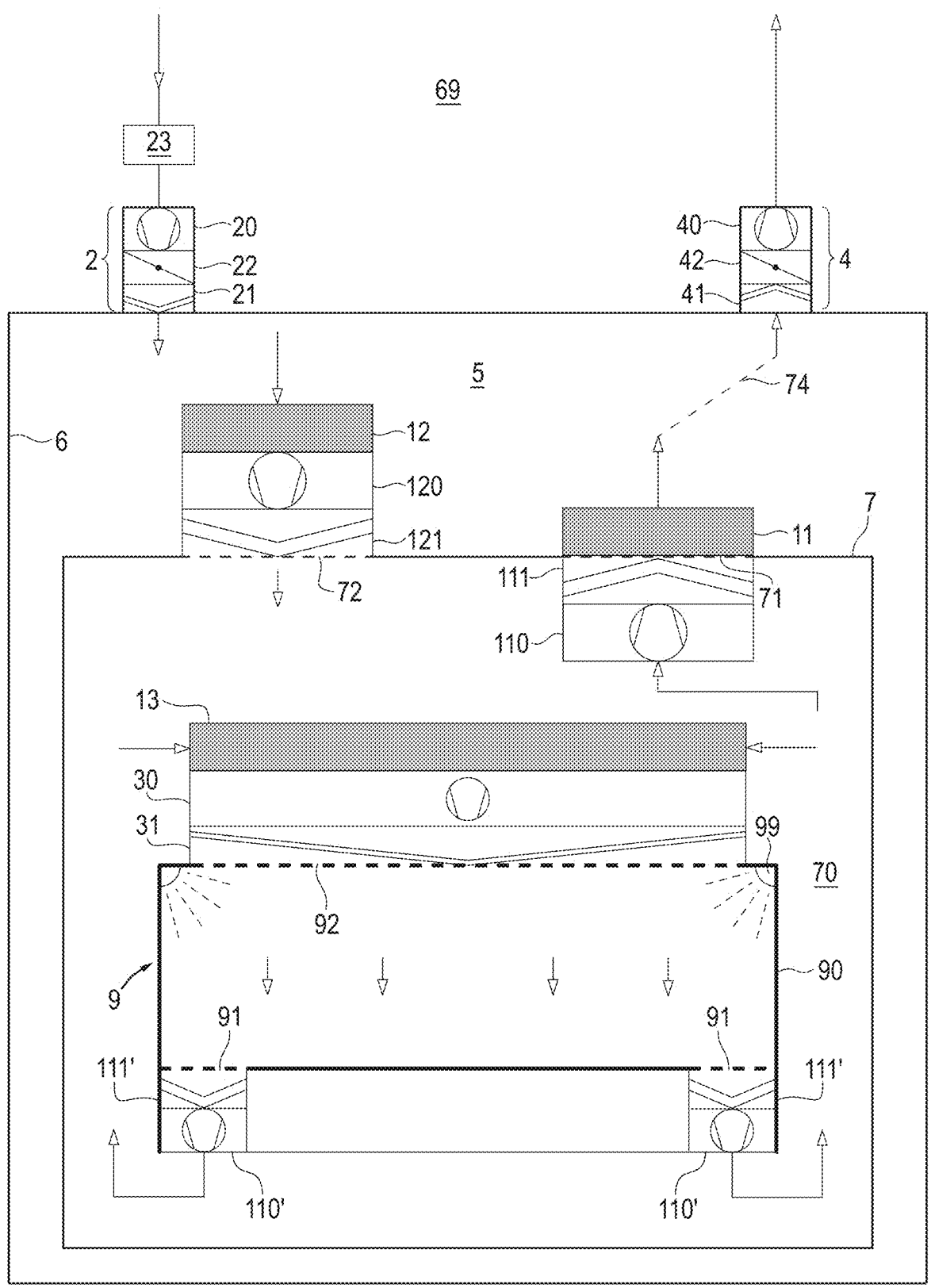
Figure 5:
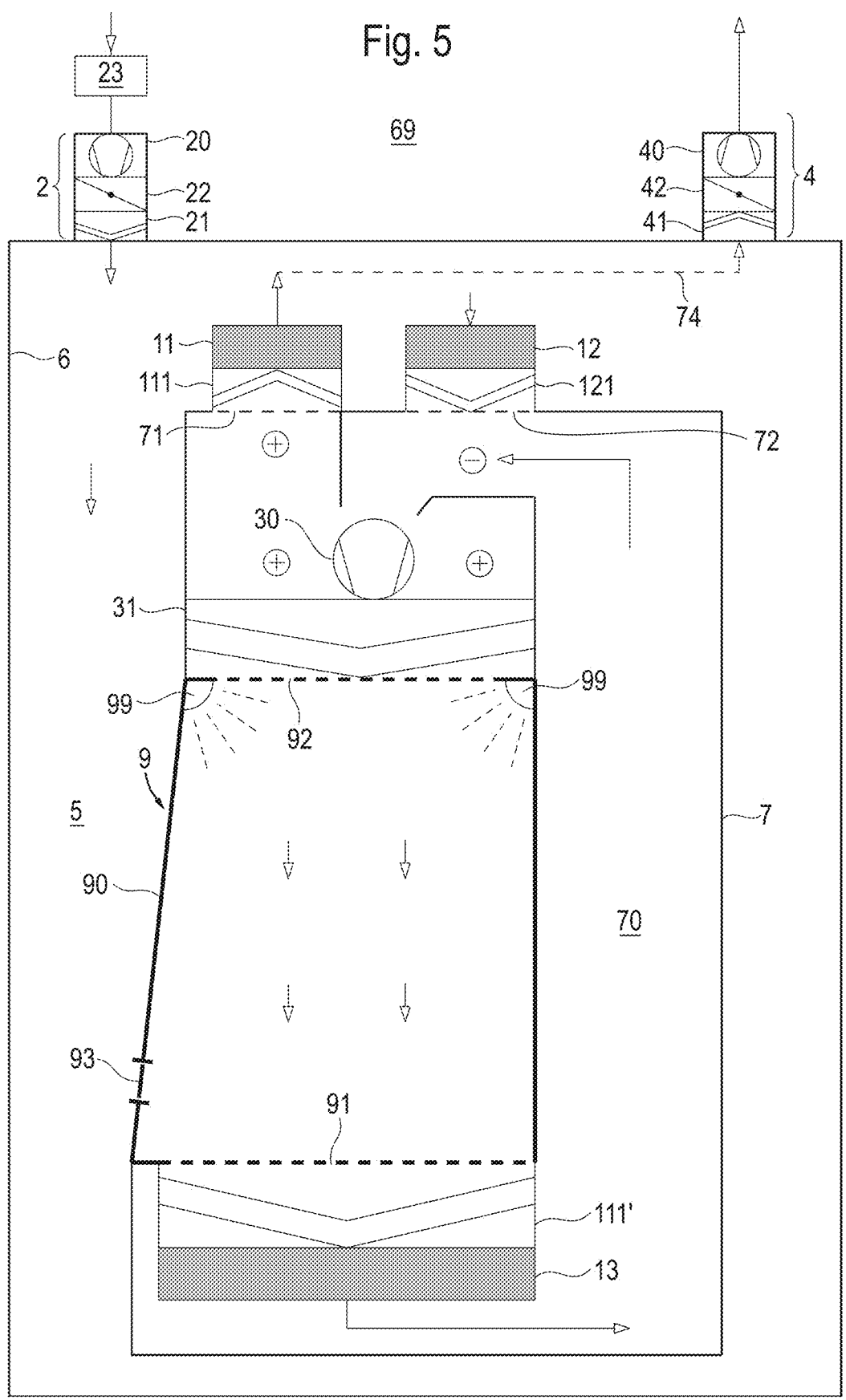
Figure 6:
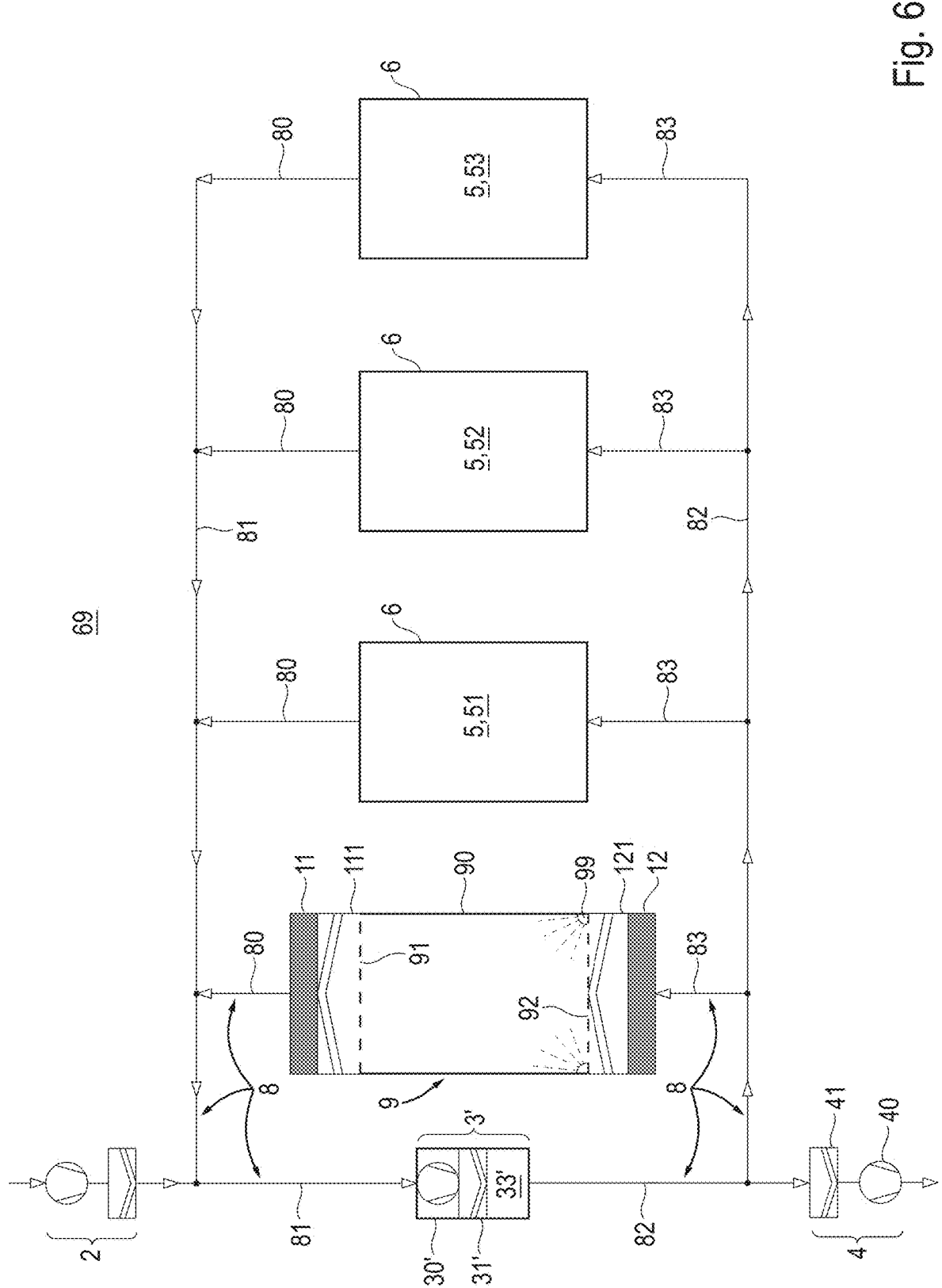
Figure 7:
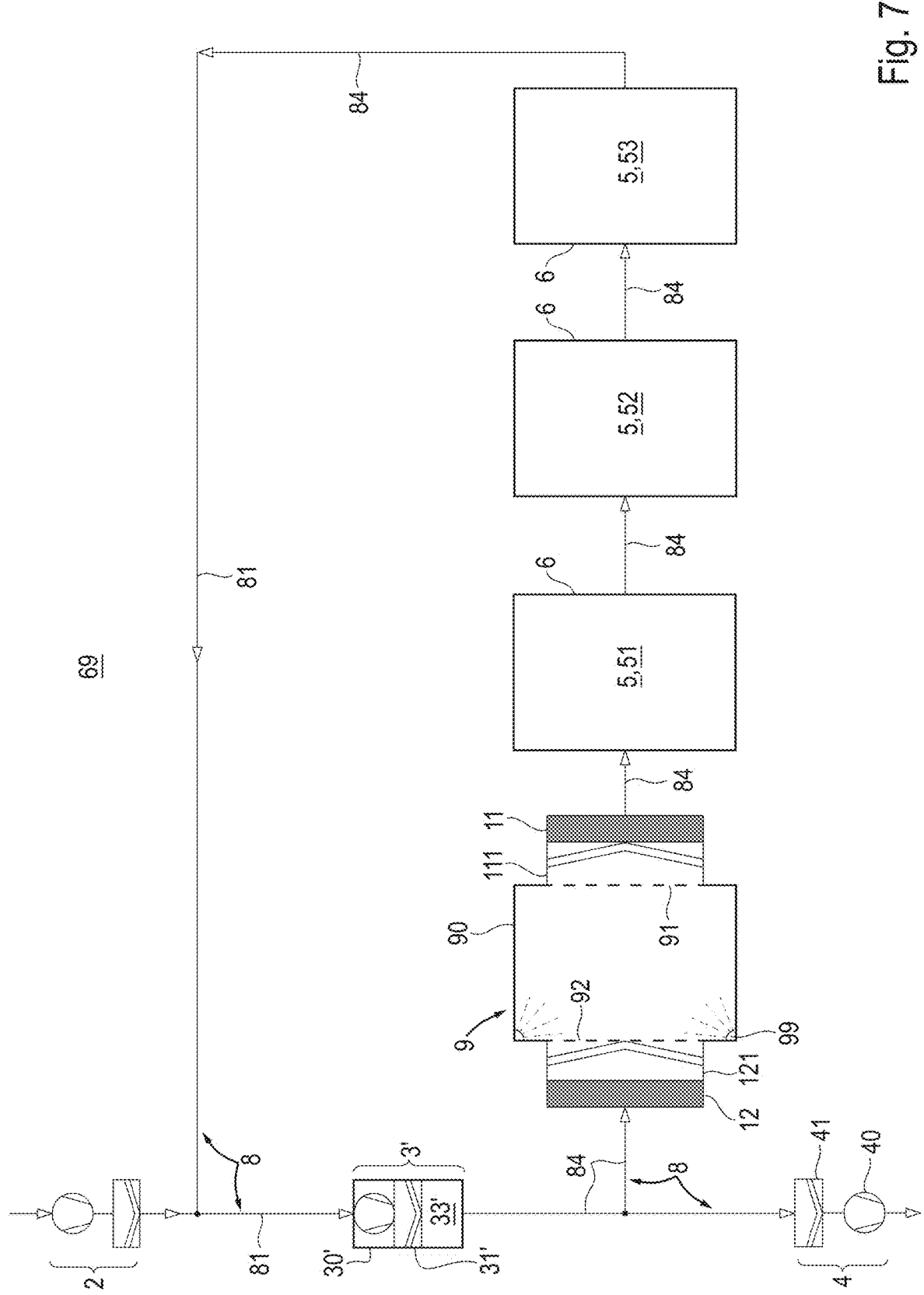
Figure 8:
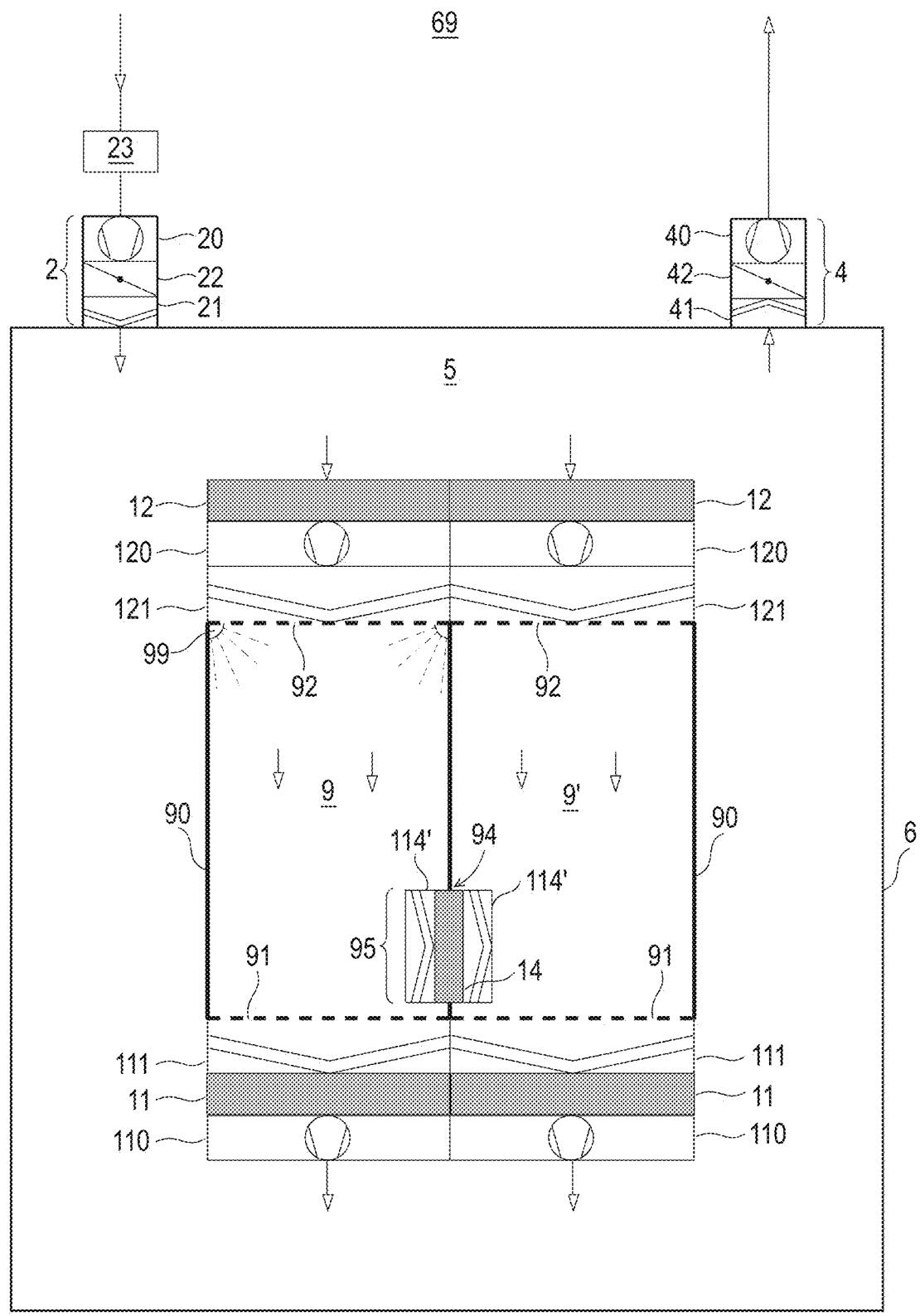

In the drawings:

FIG. 1—depicts the principle of a first embodiment arrangement according to the invention, set up in an area having a surrounding structure and having a feed air unit communicating with the open atmosphere and an exit air unit;

FIG. 2—depicts the principle of a second embodiment arrangement according to the invention, set up in an area having a surrounding structure and having a feed air unit communicating with the open atmosphere and an exit air unit;

FIG. 3—depicts the principle of a third embodiment arrangement according to the invention, set up in an area having a surrounding structure and having a feed air unit communicating with the open atmosphere and an exit air unit;

FIG. 4—depicts the principle of the FIG. 3 arrangement having an installed third catalytic unit;

FIG. 5—depicts the principle of a fourth embodiment arrangement according to the invention, in the form of a biosafety work station, set up in an area having a surrounding structure and having a feed air unit communicating with the open atmosphere and an exit air unit;

FIG. 6—depicts the principle of a fifth embodiment arrangement according to the invention, having the area structured into a plurality of space cells in parallel connection with the first containment;

FIG. 7—depicts the principle of the FIG. 6 arrangement having the space cells in series connection with the first containment; and FIG. 8—depicts the principle of the FIG. 1 arrangement having a second containment connected to the first containment and a further catalytic unit installed therebetween.

EXEMPLARY EMBODIMENT

Referring to the accompanying drawings, the detailed description follows of the arrangement which the invention provides for performing a decontamination process by means of a decontamination agent introduced into a first containment, in several embodiments and modifications thereto. The catalyst unit provided for cleaving the decontamination agent present in an at least essentially gaseous process stream is further described as a relevant apparatus of the arrangement, including various embodiments.

The following stipulation applies to the entire rest of the description. Where reference numerals appear in a drawing in order to avoid ambiguity, but are not explained in the directly related text of the description, their mention in a preceding description of a figure is incorporated by reference. In the interests of clarity, component parts are generally not designated again in subsequent figures provided it is unambiguously clear from the drawing that "recurring" component parts are concerned.

FIG. 1

In the arrangement for performing a decontamination process by means of a decontamination agent introduced into a first containment 9, the first containment 9 has a housing 90 and a primary inlet 92 for entry of a gaseous medium—conditioned air in general—and a primary outlet 91 for exit of the gaseous medium. The decontamination agent is introduced via at least one feeder 99 opening into the first containment 9. The feeder 99 is typically formed by nozzles which utilize compressed air to inject liquid decontamination agent—an aqueous hydrogen peroxide solution [$H_2O_2$] for example—into the first containment 9 in aerosol form. Useful decontamination agents having a sporicidal effect and causing at least a 3-log reduction further include, for example, nitrogen dioxide [$NO_2$] or peroxy acetic acid [$C_2H_4O_3$] or a mixture of hydrogen peroxide [$H_2O_2$] and peroxy acetic acid [$C_2H_4O_3$].

To ensure a very uniform and far-reaching importation, a plurality of feeders 99 are arranged systematically according to the size of the first containment 9. In the case of a small first containment 9, a single importation of the decontamination agent is sufficient for a decontamination following a possible preconditioning, while in the case of large first containments 9, first the bulk of the decontamination agent is introduced followed by one or more top ups according to the defined soaking time. On completion of successful soaking with the decontamination agent, a purge phase follows to export the moisture formed in the first containment 9 by flushing with air.

The primary outlet 91 is apposed by a first filter 111, which is in turn apposed by the first catalytic unit 11, which is in turn apposed by a first blower 110 conveying out of the first containment 9. The primary inlet 92 is apposed by a second filter 121, which is in turn apposed by a second blower 120 conveying into the first containment 9, followed on the upstream side by a second catalytic unit 12. This construction has a surrounding structure 6—room walls in the typical case-wich enclose an area 5. The purge gas is aspirated out of the area 5 and passes through the second catalytic unit 12 and the second filter 121 into the first containment 9—here indicated as laminar flow by pairs of perpendicular arrows. The purge gas passes through the primary outlet 91 and the subsequent first catalytic unit 11 to return into the area 5. The catalytic units 11,12 are designed to cleave the decontamination agent, so the concentration of un-degraded decontamination agent present in the gaseous medium even as it leaves the first containment 9 as a consequence of increased pressure due to introduced decontamination agent is but uncritical.

The individual catalytic unit possesses at least one catalytic element which includes a carrier consisting of aluminum ceramic or activated carbon and having silver or silver oxide or a mixture of silver and silver oxide applied thereto as catalytically active component. Alternatively, the individual catalytic unit includes at least two different catalytic elements, wherein the catalytic elements are constituted such that their respective highest efficiency in cleaving the decontamination agent occurs in different concentration ranges of the problematic components.

The employed catalytic units 11,12 degrade the decontamination agent in the permeating gaseous medium down to a concentration of below 0.5 ppm to at most 0.1 ppm. The same is achieved in the purge phase, so control valves are not required and even the purge gas may be recirculated directly into the area 5. Even personnel is therefore absolutely safe to spend long times in area 5. The air conditioning requirements of the arrangement are very greatly reduced, which also reduces the equipment requirements.

For pressure regulation and partial gas refreshening for the system, a conventional feed air unit 2 opening into the area 5 and also a conventional exit air unit 4 leading out of the area 5 are installed in the surrounding structure 6. The feed air unit 2 comprises a filter 21, a control valve 22, a blower 20 and a conditioning unit 23, which is accessed from the open atmosphere 69. The exit air unit 4 similarly consists of the filter 41, the control valve 42 and the blower 40, which opens into the open atmosphere 69.

The in-principle outcome is thus that:

- at least the primary outlet 91 is in gas communication with a first catalytic unit 11 permeated by the gaseous medium or at least the primary inlet 92 is in gas communication with a second catalytic unit 12 permeated by the gaseous medium;
- the decontamination agent introduced into the first containment 9 during the decontamination process and entering with the gaseous medium into the area 5 or the open atmosphere 69 or a second containment 9' is cleavable into uncritical components, and degradable down to an uncritical residual concentration, by the at least first and/or the at least second catalytic units 11,12; and
- at least during the period in which there is a critical concentration of the decontamination agent in the first containment 9, the first containment 9 is at all times gas pervious through the at least first and/or second catalytic units 11,12 to the area 5 or to the open atmosphere 69 or to the second containment 9' (see also FIG. 8).

FIG. 2

This arrangement solely differs from the first embodiment by the positioning of primary inlet 92 and primary outlet 91 on housing 90 and the valves 121,120,12; 11,111,110 connected thereto. Primary inlet 92 and primary outlet 91 are now no longer on the respectively upper and lower sides of the first containment 9, but are spaced apart side by side together on its upper side. The primary inlet 92 is again apposed by the second filter 121, which in turn is apposed by the second blower 120 conveying into the first containment 9 and apposed on the upstream side by the second catalytic unit 12, which extends from the area 5 to the second blower 120. Opening into area 5, the first catalytic unit 11 is connected to one side of the primary outlet 91, while the other side of the primary outlet 91 connects to the first filter 111 whereto the first blower 110 is connected on the upstream side. The arrowed trajectory in the first containment 9 now illustrates a turbulent rather than laminar gas flow.

On gaseous medium of toxic character exiting from the first catalytic unit 11, the return into the area 5 is prohibited; instead, an exit air duct 74 feeds the exit air unit 4, which has a filter 41 to retain the toxic particles and opens into the open atmosphere 69.

FIG. 3

In a modified form of the preceding embodiment, the first containment 9 with its housing 90 is now surrounded by a duct wall 7 to from a circulating air duct 70. Everything is in turn surrounded by the surrounding structure 6 in which again the feed air unit 2, including the conditioning unit 23, and the exit air unit 4 are installed. The first containment 9 continues to have the primary outlet 91 and, on the other hand, the primary inlet 92, while the duct wall 7 is provided a secondary outlet 71 and also therealongside a spaced apart secondary inlet 72. This accordingly creates fluidic communications from the primary outlet 91 to the primary inlet 92 and to the secondary outlet 71 and from the secondary inlet 72 to the primary inlet 92.

Opening out to the area 5, the first catalytic unit 11 is on its one side connected to the secondary outlet 72, while the secondary outlet 72 is apposed on its other side by the first filter 111, in turn apposed on its upstream side by the first blower 110 conveying out of the circulating air duct 70. The secondary inlet 72 is now apposed by the second filter 121, in turn apposed by the second blower 120 conveying into the circulating air duct 70 and in turn apposed on its upstream side by the second catalytic unit 12 which extends from the area 5 to the second blower 120.

The primary inlet 92 has a third filter 31 connected thereto. There is further provided a third blower 30 to convey out of the circulating air duct 70 and through the third filter 31 into the first containment 9. This third blower 30 aspirates a proportion of the gaseous medium flowing out of the primary outlet 91 of the first containment 9 for recirculation through the primary inlet 92 into the first containment 9. The first blower 110 aspirates a proportion of the gaseous medium flowing out of the primary outlet 91 of the first containment 9 for conveying into the area 5 via the first catalytic unit 11. A make-up flow through the secondary inlet 72 replaces the gas volume removed via the first blower 110. Each part of the two part primary outlet 91 present in the base of the housing 90 has an additional filter 111' connected thereto, each in turn apposed on its upstream side by an additional blower 110' conveying out of the first containment 9, through the particular additional filter 111' and finally into the circulating air duct 70.

FIG. 4

To complete the apparatus construction of FIG. 3, the pairing between the third filter 31 and the third blower 30 is assigned a third catalytic unit 31 which extends from the circulating air duct 70 and is connected to the third blower 30.

FIG. 5

This arrangement about the first containment 9 takes the form of a biosafety work station installed in an area 5 surrounded by a surrounding structure 6 and having a feed air unit 2 (including a conditioning unit 23) in communication with the open atmosphere 69 and an exit air unit 4.

The first containment 9 with its housing 90 is in turn surrounded by a duct wall 7 to form the circulating air duct 70. The frontal side of the housing 90 typically has a sealable window 93 to permit reaching into the first containment 9. The secondary outlet 71 and the secondary inlet 72 sit in the duct wall 7. This creates fluidic communications from the primary outlet 91 to the primary inlet 92 and to the secondary outlet 71 and from the secondary inlet 72 to the primary inlet 92. The secondary outlet 71 has connected to it the first filter 111 apposed on its upstream side by the first catalytic unit 11 for gaseous medium to flow through into the area 5. The secondary inlet 72 has connected to it the second filter 121 apposed on its upstream side by the second catalytic unit 12 for gaseous medium to flow through out of the area 5. A third filter 31 is connected to the primary inlet 92.

There is further provided a third blower 30 for conveying through the secondary inlet 72 out of the area 5 and out of the circulating air duct 70 and through the third filter 31 into the first containment 9. The third blower 30 further conveys proportions of the gaseous medium flowing out of the primary outlet 91 of the first containment 9 and routed via the circulating air duct 70 to flow respectively back into the first containment 9 and through the secondary outlet 71 to the area 5. In addition, an additional filter 111' is connected to the primary outlet 91 and apposed on its upstream side by a third catalytic unit 13 opening out into the circulating air duct 70. The plus signs and the minus sign in the circulating air duct symbolize the pressure conditions prevailing there as respectively overpressure and underpressure.

FIG. 6

The area 5; 51-53 here subdivides into a plurality of space cells 51-53, wherein each space cell 51-53 is delimited by its particular surrounding structure 6 from the surrounding environment 69. The space cells 51-53 are connected by a duct grid 8 to the first containment 9 in parallel. Like hereinabove, the first containment 9 has its housing, the primary outlet 91 and the primary inlet 92 and also feeders 99 to import the decontamination agent.

An air supply unit 3' for circulating the gaseous medium through the first containment 9 and the space cells 51-53 is installed in the duct grid 8. The air supply unit 3' comprises a supply blower 30', a supply filter 31' and a conditioning unit 33'. A first filter 111 is disposed between the primary outlet 91 and one side of the first catalytic unit 11 wherethrough gaseous medium flowing back out of the first containment 9 passes into the duct grid 8. A second filter 121 is disposed between the primary inlet 92 and one side of the second catalytic unit 12 wherethrough gaseous medium passes out of the duct grid 8 into the first containment 9. The feed air unit 2 aspirating gaseous medium out of the open atmosphere 69 serves to import fresh air into the duct grid 8 and an exit air unit 4 is connected to the duct grid 8 and serves to export exit air into the open atmosphere 69. An outlet duct 80 from the first catalytic unit 11 and from each space cell 51-53 opens into a return duct 81 which leads to the air supply unit 3'. An inlet duct 83 extends in each case to the second catalytic unit 12 and to each space cell 51-53 from a forerun duct 82, the forerun duct 82 emanating from the air supply unit 3'.

FIG. 7

In a modified form of the preceding embodiment, the space cells 51-53 connected by a duct grid 8 to the first containment 9 are now arranged in series. A communicating duct 84 now extends from the first catalytic unit 11 to a neighboring space cell 51 and also between pairs of neighboring space cells 51,52; 52,53 and a communicating duct 84 from a rearmost space cell 53 opens into a return duct 81 leading to the air supply unit 3'. Further a separate communicating duct 84 emanates from the air supply unit 3' to extend to the second catalytic unit 12.

FIG. 8

This arrangement is closely related to the embodiment of FIG. 1, except that the first containment 9 is connected to a second containment 9' with a further catalytic unit 14 installed therebetween. The first containment 9, which is for performing a decontamination process with decontamination agent to be introduced, has an opening 94 in its housing 90. The further catalytic unit 14 is disposed in this opening 94 and here opens out into the second containment 9'. Alternatively, the further catalytic unit 14 could open into the area 5 or the open atmosphere 69. The further catalytic unit 14 is assigned a further filter 114' on both the side of the first containment 9 and the side of the second containment 9'. Preferably, the construction formed from the further catalytic unit 14 and the further filters 114' has the shape of a door 95 which can be opened to transfer ware between the first containment 9 and the second containment 9'.

The functional principle applicable here is again that at least during the period in which there is a critical concentration of the decontamination agent in the first containment 9, the first containment 9 is at all times gas pervious through the further catalytic unit 14 to the second containment 9'.

The specific features of the essential apparatuses for the catalytic units 11-14 forming the arrangement make possible that a) the decontamination agent in the gaseous medium entering the area 5; 51-53 or the second containment (9') or into the open atmosphere 69 has an uncritical concentration of non-degraded decontamination agent amounting to less than 0.5 ppm, whereas a concentration above 1.0 ppm is defined as critical; wherein preferably:

b) the attained uncritical concentration of non-degraded decontamination agent is not more than 0.1 ppm.

In its first configuration, the at least first catalytic unit 11 and, if respectively present, preferably also the second, third and further catalytic units 12,13,14 have at least one catalytic element consisting of:

a) a carrier material formed from aluminum ceramic or activated carbon; and b) a catalytically active component applied to the carrier material by chemical plating and taking the form of nanoparticles formed from silver or silver oxide or a mixture of silver and silver oxide.

The catalytically active component comprises from 0.05 wt % up to 0.5 wt %, preferably at 0.1 wt %, of the carrier material in the at least one catalytic element. The at least one catalytic element has a catalytically effective surface area ranging up to 320 $m^2$ per gram of catalyst material used, being the combination of carrier material plus applied catalytically active component. Here the specific surface area [$m^2$ per gram] of the catalyst material used, being the combination of carrier material plus applied catalytically active component, is not decreased by the applied nanoparticles in relation to the specific surface area [$m^2$ per gram] of the carrier material alone, before application of nanoparticles.

In its second configuration, the at least first catalytic unit 11 and, if respectively present, preferably also the second, third and further catalytic units 12,13,14 have at least two different catalytic elements, wherein the catalytic elements are constituted such that their respective highest efficiency in cleaving the decontamination agent occurs in different concentration ranges of the decontamination agent.

The at least two different catalytic elements of the catalytic units 11-14 are formed by:

a) different catalytically active components applied to identical carrier material by chemical plating; and/or b) identical catalytically active component applied to different carrier materials by chemical plating.

A first catalytic element of the at least two different catalytic elements has aluminum ceramic or activated carbon as carrier material and manganese oxide or Prussian Blue [iron(III) hexacyanidoferrate(II/III)] as catalytically active component applied to the carrier material in the form of nanoparticles. A second catalytic element of the at least two different catalytic elements has aluminum ceramic or activated carbon as carrier material and silver or silver oxide or a mixture of silver and silver oxide applied as catalytically active component to the carrier material in the form of nanoparticles.

Again, the catalytically active component comprises from 0.05 wt % up to 0.5 wt %, preferably at 0.1 wt %, of the carrier material in the particular catalytic element. The particular catalytic element has a catalytically effective surface area ranging up to 320 $m^2$ per gram of catalyst material used, being the combination of carrier material plus applied catalytically active component. Again, the specific surface area [$m^2$ per gram] of the catalyst material used, being the combination of carrier material plus applied catalytically active component, is not decreased by the applied nanoparticles in relation to the specific surface area [$m^2$ per gram] of the carrier material alone, before application of nanoparticles.

Manganese oxide or Prussian Blue [iron(III) hexacyanidoferrate(II/III)] is employed as catalytically active component for a first catalytic element to degrade decontaminant in the range of a first concentration. By contrast, silver or silver oxide or a mixture of silver and silver oxide is employed as catalytically active component for a second catalytic element to degrade decontamination agent in the range of a second concentration, which is lower than the first concentration.

The invention claimed is:

1. An arrangement for performing a decontamination process by means of a decontamination agent introduced into a first containment, wherein:
the first containment has a housing;
the housing has a primary inlet for entry of a gaseous medium into the first containment;
the primary inlet of the first containment leads to an area external to the first containment or into open atmosphere or to a second containment;
the housing has a primary outlet for exit of the gaseous medium out of the first containment;
the primary outlet of the first containment leads to an area external to the first containment or into the open atmosphere or to the second containment;
at least the primary outlet is in gas communication with a first catalytic unit permeated by the gaseous medium;
the primary inlet is in gas communication with a second catalytic unit permeated by the gaseous medium;
the decontamination agent introduced into the first containment during the decontamination process and entering with the gaseous medium into the area or the open atmosphere or the second containment is cleavable into uncritical components, and degradable down to an uncritical residual concentration, by the first and second catalytic units; and
at least during the period in which there is a critical concentration of the decontamination agent in the first containment, the first containment is at all times gas pervious through the first and second catalytic units to the area or to the open atmosphere or to the second containment.

2. The arrangement as claimed in claim 1, wherein
at least the first catalytic unit is assigned a first filter or at least the second catalytic unit is assigned a second filter; and
the pairings between the first catalytic unit and the first filter and between the second catalytic unit and the second filter are assigned respectively a first and a second blower.

3. The arrangement as claimed in claim 1, wherein
the first containment with its housing is surrounded by a duct wall having a secondary outlet and a secondary inlet to form a circulating air duct having fluidic communication from the primary outlet to the primary inlet and to the secondary outlet and also from the secondary inlet to the primary inlet;
the first catalytic unit is connected to the secondary outlet; and
the second catalytic unit is connected to the secondary inlet.

4. The arrangement as claimed in claim 3, wherein
the first catalytic unit is assigned the first filter and the first blower;
the second catalytic unit is assigned the second filter and the second blower;
at least one third filter is connected to the primary inlet;
at least one third blower is arranged to convey out of the circulating air duct, through the at least one third filter and into the first containment;
the at least one third blower aspirates a portion of the gaseous medium flowing out of the primary outlet of the first containment for recirculation through the primary inlet into the first containment, while the first blower aspirates a proportion of the gaseous medium flowing out of the primary outlet of the first containment for conveying into the area via the first catalytic unit; and
a make-up flow through the secondary inlet replaces the gas volume removed via the first blower.

5. The arrangement as claimed in claim 4, wherein
at least one additional filter is connected between the primary outlet and the circulating air duct, and
at least one additional blower is connected to the at least one additional filter.

6. The arrangement as claimed in claim 4, wherein the pairing between the at least one third filter and the at least one third blower is assigned a third catalytic unit.

7. The arrangement as claimed in claim 1, wherein
the first containment with its housing is surrounded by a duct wall having a secondary outlet and a secondary inlet to form a circulating air duct having fluidic communication from the primary outlet to the primary inlet and to the secondary outlet and also from the secondary inlet to the primary inlet;
the secondary outlet has connected to it the first filter which is assigned the first catalytic unit for gaseous medium to flow through into the area;
the secondary inlet has connected to it the second filter which is assigned the second catalytic unit for gaseous medium to flow through out of the area;
a third filter is connected to the primary inlet;
a third blower is provided for conveying through the secondary inlet out of the area and out of the circulating air duct and through the third filter into the first containment;
the third blower further conveys proportions of the gaseous medium flowing out of the primary outlet of the first containment and routed via the circulating air duct to flow respectively back into the first containment and through the secondary outlet to the area; and
at least one additional filter is connected to the primary outlet.

8. The arrangement as claimed in claim 7, wherein a third catalytic unit is disposed in the circulating air duct.

9. The arrangement as claimed in claim 1, wherein
the area is delimited by a surrounding structure from a surrounding environment; and
the area has connected to it a feed air unit for importing conditioned fresh air into the area and also an exit air unit for exporting exit air out of the area.

10. The arrangement as claimed in claim 1, wherein
the area subdivides into a plurality of space cells, such that a respective space cells is delimited by its particular surrounding structure from a surrounding environment;
the space cells are connected by a duct grid to the first containment in parallel or series; and
at least one air supply unit for circulating the gaseous medium through the first containment and the space cells is installed in the duct grid.

11. The arrangement as claimed in claim 10, wherein
at least one first filter is disposed between the primary outlet and one side of the first catalytic unit wherethrough gaseous medium flowing back out of the first containment passes into the duct grid; and/or at least one second filter is disposed between the primary inlet and one side of a second catalytic unit wherethrough gaseous medium passes out of the duct grid into the first containment.

12. The arrangement as claimed in claim 10, wherein
the air supply unit comprises a supply blower, a supply filter and a conditioning unit;
a feed air unit aspirating gaseous medium out of the open atmosphere serves to import fresh air into the duct grid and an exit air unit is connected to the duct grid and serves to export exit air into the open atmosphere; wherein:
in the case of a parallel connection:
   an outlet duct from the first catalytic unit and from each space cell opens into a return duct which leads to the air supply unit; and
   an inlet duct extends in each case to the second catalytic unit and to each space cell from a forerun duct emanating from the air supply unit; or
in a series connection:
   a communicating duct extends from the first catalytic unit to a neighboring space cell and also between pairs of neighboring space cells and a communicating duct from a rearmost space cell opens into the return duct leading to the air supply unit; and
   a separate communicating duct emanates from the air supply unit to extend to the second catalytic unit.

13. The arrangement as claimed in claim 1, wherein
the first containment, which is for performing a decontamination process with decontamination agent to be introduced, has an opening in its housing;
a further catalytic unit is installed in the opening;
the further catalytic unit opens into the second containment or the area or the open atmosphere; and
at least during the period in which there is a critical concentration of the decontamination agent in the first containment, the first containment is at all times gas pervious through the further catalytic unit to the second containment or to the area or to the open atmosphere.

14. The arrangement as claimed in claim 13, wherein
the further catalytic unit is assigned a further filter at least aside the first containment or the second containment or the area or the open atmosphere; and
the pairing between further catalytic unit and the at least one further filter has the shape of a door which can be opened to transfer ware between the first containment and the second containment or the area or the open atmosphere.

15. The arrangement as claimed in claim 1, wherein gaseous medium of toxic character exiting from the first catalytic unit does not have any access into the area but passes via an exit air duct to the exit air unit which includes a filter to retain the toxic particles and opens into the open atmosphere.

16. The arrangement as claimed in claim 1 wherein the containments are configured to be
isolators, for example for the pharmaceutical-chemical industry, locks and safety work stations, for example for microbiological operations or operations involving toxic entities; and
restricted access barrier systems so-called RABSs, including mobile and stationary type, such as means of transport and for treatment of patients, and also production rooms and laboratories.

17. The arrangement as claimed in claim 1, wherein
the decontamination agent used has a sporicidal effect which causes at least a 3-log reduction, passes in aerosol form into the containment, and may be one of hydrogen peroxide $[H_2O_2]$ and nitrogen dioxide $[NO_2]$ and peroxy acetic acid $[C_2H_4O_3]$ and a mixture of hydrogen peroxide $[H_2O_2]$ and peroxy acetic acid $[C_2H_4O_3]$.

18. The arrangement as claimed in claim 1, wherein
the decontamination agent in the gaseous medium entering the area or the second containment or into the open atmosphere has an uncritical concentration of non-degraded decontamination agent amounting to less than 0.5 ppm, whereas a concentration above 1.0 ppm is defined as critical; and
the attained uncritical concentration of non-degraded decontamination agent is not more than 0.1 ppm.

19. The arrangement as claimed in claim 1, wherein
the at least first catalytic unit and, if respectively present, preferably also the second, third and further catalytic units have at least one catalytic element consisting of:
a carrier material formed from aluminum ceramic or activated carbon; and
a catalytically active component applied to the carrier material by chemical plating and taking the form of nanoparticles formed from silver or silver oxide or a mixture of silver and silver oxide.

20. The arrangement as claimed in claim 19, wherein
the catalytically active component comprises from 0.05 wt % up to 0.5 wt %, of the carrier material in the at least one catalytic element;
the at least one catalytic element has a catalytically effective surface area ranging up to 320 $m^2$ per gram of catalyst material used, being the combination of carrier material plus applied catalytically active component; and
the specific surface area [$m^2$ per gram] of the catalyst material used, being the combination of carrier material plus applied catalytically active component, is not decreased by the applied nanoparticles in relation to the specific surface area [$m^2$ per gram] of the carrier material alone, before application of nanoparticles.

21. The arrangement as claimed in claim 1, wherein the at least first catalytic unit and, if respectively present, the second, third and further catalytic units have at least two different catalytic elements, the catalytic elements being constituted such that their respective highest efficiency in cleaving the decontamination agent occurs in different concentration ranges of the decontamination agent.

22. The arrangement as claimed in claim 21, wherein
the at least two different catalytic elements of the catalytic units are formed by
different catalytically active components applied to identical carrier material by chemical plating; and/or
identical catalytically active component applied to different carrier materials by chemical plating, wherein
a first catalytic element of the at least two different catalytic elements has aluminum ceramic or activated carbon as carrier material and manganese oxide or Prussian Blue [iron(III) hexacyanidoferrate(II/III)] as catalytically active component applied to the carrier material in the form of nanoparticles; and
a second catalytic element of the at least two different catalytic elements has aluminum ceramic or activated carbon as carrier material and silver or silver oxide or a mixture of silver and silver oxide applied as catalytically active component to the carrier material in the form of nanoparticles.

23. The arrangement as claimed in claim 22, wherein the catalytically active component comprises from 0.05 wt % up to 0.5 wt % of the carrier material in the particular catalytic element;

the particular catalytic element has a catalytically effective surface area ranging up to 320 m² per gram of catalyst material used, being the combination of carrier material plus applied catalytically active component; and the specific surface area [m² per gram] of the catalyst material used, being the combination of carrier material plus applied catalytically active component, is not decreased by the applied nanoparticles in relation to the specific surface area [m² per gram] of the carrier material alone, before application of nanoparticles.

24. The arrangement as claimed in claim 21, wherein manganese oxide or Prussian Blue [iron(III) hexacyanidoferrate(II/III)] is employed as catalytically active component for a first catalytic element to degrade decontamination agent in the range of a first concentration; and silver or silver oxide or a mixture of silver and silver oxide is employed as catalytically active component for a second catalytic element to degrade decontamination agent in the range of a second concentration, which is lower than the first concentration.

* * * * *